United States Patent
Bale

(10) Patent No.: US 6,808,717 B1
(45) Date of Patent: Oct. 26, 2004

(54) AEROSOL COOLANT SPRAY FOR KILLING AND REMOVING TICKS

(76) Inventor: Isidore Bale, 20 Meridian Rd. #9, Eatontown, NJ (US) 07724

( * ) Notice: Subject to any disclaimer, the term of this patent is extended or adjusted under 35 U.S.C. 154(b) by 0 days.

(21) Appl. No.: 10/445,148

(22) Filed: May 23, 2003

(51) Int. Cl.$^7$ ............................................. A01N 25/00
(52) U.S. Cl. .................... 424/405; 424/45; 424/409; 424/725; 424/736; 424/745; 424/747
(58) Field of Search ................ 424/45, 405, 409, 424/725, 736, 745, 747

(56) References Cited

U.S. PATENT DOCUMENTS 4,834,967 A * 5/1989 Locicero ..................... 424/45

* cited by examiner

Primary Examiner—Michael G. Hartley
Assistant Examiner—Konata M. George
(74) Attorney, Agent, or Firm—Ezra Sutton

(57) ABSTRACT

A composition of an aerosol coolant spray for killing and removing ticks from human skin, to be dispensed from a pressurized a pressurized aerosol spray cannister. The aerosol coolant spray composition includes a liquid coolant material for freezing the essential oil, and the cooled essential oil is used for immobilizing and killing the tick on the skin of a human. The aerosol coolant spray composition further includes a diluent material being used as a carrier material for emulsifying the essential oil and the coolant material within the pressurized aerosol spray cannister.

36 Claims, 2 Drawing Sheets

The tick begins its meal, alternating between drawing blood and injecting saliva.

AEROSOL COOLANT SPRAY FOR KILLING AND REMOVING TICKS

FIELD OF THE INVENTION

The present invention relates to an aerosol coolant spray for killing and removing ticks. More particularly, the aerosol coolant spray composition includes a coolant material, an essential oil and a diluent material.

BACKGROUND OF THE INVENTION

The family IXODOIDEA includes ticks which are wingless, blood sucking arachnids. The term "tick" also includes two winged parasitic insects. Ticks are parasitic and infect mammals including humans and warm blooded animals.

Traditional methods for treatment and removal of ticks from humans present many problems. These methods of treatment include the use of tick shampoos and soaps, asphyxiation and/or heat. The use of tick shampoos and soaps on humans requires a substantial exposure to harsh chemicals which effect the human skin with rashes, hives and/or eczema. Failure to allow the soap or shampoo to remain in contact with the skin for the prescribed amount of time may result in the tick(s) remaining attached to the human skin, which can lead to infections such as lyme disease.

Additionally, tick removal from humans has also been accomplished by coating the tick with grease, vaseline or nail polish to bring about asphyxiation of the tick. Also, ticks have been removed by touching the head of the tick with a hot match. The aforementioned methods are messy, time consuming, as well as dangerous in the latter case. Further, the mouth parts of the tick may remain in the human skin and become sites of infection as previously indicated causing various skin problems.

DESCRIPTION OF THE PRIOR ART

Aerosol sprays for killing, repelling and removing ticks from human skin including refrigerants, anesthetic compounds or essential oil within the aerosol cannister have been generally disclosed in the prior art. For example, U.S. Pat. No. 4,834,967 to Locicero discloses a compressible liquid refrigerant in aerosol form to freeze, kill and dislodge a tick from the skin of a user.

U.S. Pat. No. 5,106,622 to Sherwood et al. discloses a repellent composition containing natural essential oils such as citronella, cedar and wintergreen to produce an environmentally safe, topical pest repellent which is effective against ticks.

U.S. Pat. No. 5,414,014 to Schneider et al. discloses an insect repellent composition having one or more anesthetic compounds for facilitating the removal of ticks from the human dermis. The composition also includes a skin permeability enhancing carrier, an anti-inflammatory agent, an antibiotic and an insect repellent.

None of the prior art references teach or disclose the composition of an aerosol coolant spray for killing and removing ticks of the present invention having a coolant material, an essential oil and a diluent material in order to kill and remove ticks in a safe, quick, and efficient manner.

Accordingly, it is an object of the present invention to provide a composition of an aerosol coolant spray for killing and removing ticks from human skin being dispensed from a pressurized aerosol spray cannister.

Another object of the present invention is to provide an aerosol spray composition that consists of a liquid coolant material, an essential oil and a diluent material which allows the safe, quick, painless and efficient killing and removal of ticks from human skin.

Another object of the present invention is to provide an aerosol spray composition for killing and removing ticks from human skin without any deleterious or harmful effect on the human skin of the user.

Another object of the present invention is to provide an aerosol spray composition for killing and removing ticks from an area of human skin wherein the liquid coolant material cools the essential oil which is applied to the tick so as to freeze, kill and dislodge the tick from the specific area of skin that is affected.

Another object of the present invention is to provide an aerosol spray composition for killing and removing ticks from a specific area of human skin wherein a compressible liquid coolant material and an essential oil are in aerosol form for spraying the cooled essential oil directly on the tick so as to freeze, kill and dislodge the tick from the skin of the user without freezing or damaging the skin of the user.

A further object of the present invention is to provide a pressurized aerosol coolant spray composition for killing and removing ticks from a pressurized aerosol spray cannister that can be mass produced in an automated and economical manner and is readily affordable by the consumer.

SUMMARY OF THE PRESENT INVENTION

In accordance with the present invention, there is provided a composition of an aerosol coolant spray for killing and removing ticks from human skin, to be dispensed from a pressurized aerosol spray cannister. The aerosol coolant spray composition includes a liquid coolant material for freezing the essential oil and the cooled essential oil kills the tick on the skin of a human. The aerosol coolant spray composition further includes a diluent material being used as a carrier material for emulsifying the essential oil and the coolant material within the pressurized aerosol spray cannister.

The liquid coolant material is selected from the group consisting of chloroform, ether, fluorocarbon refrigerant R134, liquid air, liquid argon, liquid butane, liquid carbon dioxide, liquid DYMEL™ (dimethyl ether; E.I. DuPont de Nemours and Co. bend, liquid helium, liquid nitrogen, liquid oxygen, liquid propane, and other liquid refrigerant compounds, and coolant materials.

The essential oil is selected from the group consisting of cedar oil, citronella oil, wintergreen oil, pennyroyal, olive oil, eucalyptus oil, geranium oil, rosemary oil, peppermint oil, lavender oil, spearmint oil, pine needle oil, lemon oil, D-limonene, grapefruit oil, lavandin oil, cinnamon oil, clove oil, thyme oil, lemon grass oil, mandarin oil, tangerine oil, orange oil, citrus oil, lime oil, coriander oil, pomegranate oil, walnut oil, peanut oil, corn oil, canola oil, sunflower oil, sesame oil, linseed oil, safflower oil and terpenes.

The diluent material is selected from the group consisting of pectin, gum arabic, trasazapthenth, lecithin, polysorbate 20, polysorbate 60, polysorbate 80, stearic acid, glyceryl cocoate, sorbitan stearate, alginate, sunflower ceramides, guar vegetable gum, xanthen vegetable gum and other naturally occurring emulsifiers.

BRIEF DESCRIPTION OF THE DRAWINGS

Further objects, features, and advantages of the present invention will become apparent upon the consideration of the following detailed description of the presently-preferred embodiment when taken in conjunction with the accompanying drawings, wherein.

DETAILED DESCRIPTION OF THE EMBODIMENTS

Figure 1:
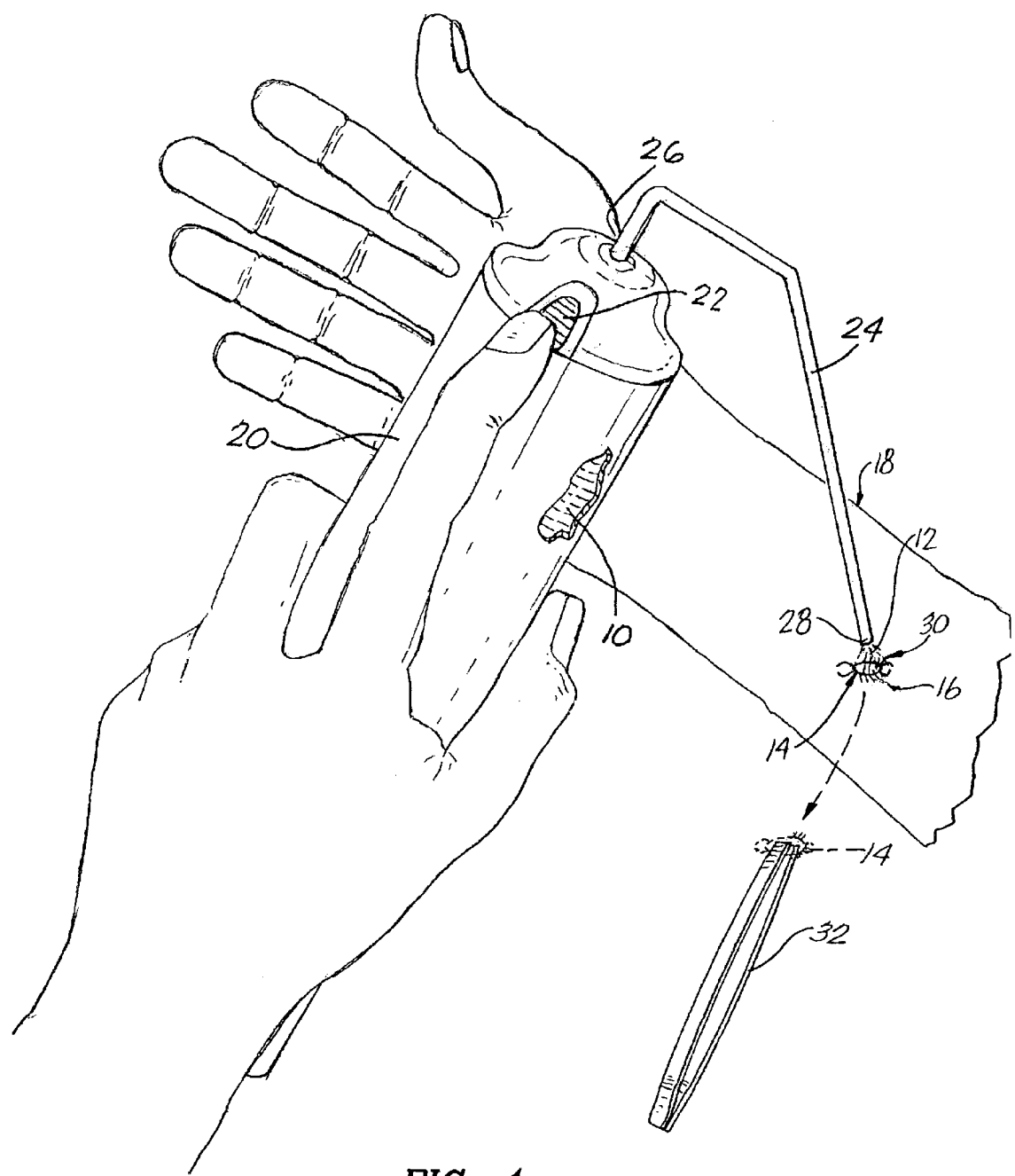
FIG. 1 is a perspective view of the pressurized aerosol spray cannister containing the aerosol coolant spray composition of the present invention showing the aerosol coolant spray composition in operational use being sprayed on a tick attached to the surface of human skin.

The present invention provides for a composition 10 of an aerosol liquid coolant spray 12 for killing and removing ticks 14 from the skin surface 16 of a human 18, as depicted in FIG. 1 of the drawings, wherein the tick 14 may be located on various parts of the human anatomy 18 (i.e. arms, legs, feet, chest, etc). The aerosol liquid coolant spray 12 is to be dispensed from a pressurized aerosol spray cannister 20. The aerosol liquid coolant spray composition 10 includes a liquid coolant material for cooling an essential oil. The cooled essential oil is then sprayed onto the affected area of human skin to immobilize and kill the tick on human skin. The aerosol coolant spray composition further includes a diluent material being used as a carrier material for emulsifying the essential oil and the coolant material within the pressurized aerosol spray cannister 20. Optionally, the aerosol liquid coolant spray composition 10 may also include a fragrance for scenting the composition 10 when applied to the skin surface 16 of the user 18.

The liquid coolant material is selected from the group consisting of chloroform, ether, fluorocarbon refrigerant R134, liquid air, liquid argon, liquid butane, liquid carbon dioxide, liquid DYMEL ™ (dimethyl ether; E.I. DuPont de Nemours and Co.) blend, liquid helium, liquid nitrogen, liquid oxygen, liquid propane, and other liquid refrigerant compounds, or coolants. (See Table 1). The liquid coolant material has a boiling point in the range of −340° F. to −20° F. The liquid coolant material is in the range of 30.0% to 45.0% by weight of the total composition 10.

The essential oil is selected from the group consisting of cedar oil, citronella oil, wintergreen oil, pennyroyal, olive oil, eucalyptus oil, geranium oil, rosemary oil, peppermint oil, lavender oil, spearmint oil, pine needle oil, lemon oil, D-limonene, grapefruit oil, lavandin oil, cinnamon oil, clove oil, thyme oil, lemon grass oil, mandarin oil, tangerine oil, orange oil, citrus oil, lime oil, coriander oil, pomegranate oil, walnut oil, peanut oil, corn oil, canola oil, sunflower oil, sesame oil, linseed oil, safflower oil and terpenes. (See Table 2). Terpenes can include orange terpenes, lemon terpenes, mandarin terpenes, tangerine terpenes and lime terpenes. One or more of the essential oils maybe used within the composition 10. The essential oil 10 is in the range of 40.0% to 55.0% by weight of the total composition.

The diluent material is selected from the group consisting of pectin, gum arabic, trasazapthenth, lecithin, polysorbate 20, polysorbate 60, polysorbate 80, stearic acid, glyceryl cocoate, sorbitan stearate, alginate, sunflower ceramides, guar vegetable gum, xanthen vegetable gum and other naturally occurring emulsifiers. (See Table 3). One or more of the diluent materials may be used within the composition 10. The diluent material is in the range of 0.10% to 10.0% by weight of the total composition.

The fragrances are selected from the group consisting of neroli oil, anethole, rose oil, methylene, sandal wood, musk, patchouly, citronella, eucalyptus, lemon grass, lavender, kamaus, cedarwood, geranium, chamomile and spruce (See Table 4). The fragrance is in the range of 0.10 to 2.0% by weight of the total composition

TABLE 1

LIQUID COOLANT MATERIALS

| | |
|---|---|
| chloroform | liquid DYMEL ™ blend |
| ether | liquid helium |
| fluorocarbon refrigerant R134 | liquid nitrogen |
| liquid air | liquid oxygen |
| liquid argon | liquid propane |
| liquid butane | liquid refrigerant compounds and |
| liquid carbon dioxide | other coolant formulations |

TABLE 2

NATURAL ESSENTIAL OILS

| | | |
|---|---|---|
| canola oil | lavandin oil | pomegranate oil |
| cedar oil | lavender oil | rosemary oil |
| cinnamon oil | lemon oil | spearmint oil |
| citronella oil | lemon grass oil | safflower oil |
| citrus oil | lime oil | sesame oil |
| clove oil | linseed oil | sunflower oil |
| coriander oil | mandarin oil | tangerine oil |
| corn oil | olive oil | terpenes |
| D-limonene | orange oil | thyme oil |
| eucalyptus oil | pennyroyal | walnut oil |
| geranium oil | peppermint oil | wintergreen oil |
| grapefruit oil | pine needle oil | |

TABLE 3

NATURAL DILUENT CARRIER MATERIALS

| | |
|---|---|
| alginate | polysorbate 60 |
| glyceryl cocoate | polysorbate 80 |
| guar vegetable gum | sorbitan stearate |
| gum arabic | stearic acid |
| lecithin | sunflower ceramides |
| pectin | trasazapthenth |
| polysorbate 20 | xanthen vegetable gum |

TABLE 4

FRAGRANCES

| | |
|---|---|
| anethole | methylene |
| cedarwood | musk |
| chamomile | neroli oil |
| citronella | patchouly |
| eucalyptus | rose oil |
| geranium | sandal wood |
| kamaus | spruce |
| lavender | |

| INGREDIENT | BY WEIGHT PERCENTAGES (%) |
|---|---|
| EMBODIMENT 1 | |
| Flourocarbon refrigerant R134 | 30.0% to 45.0% |
| Cedar oil | 40.0% to 55.0% |
| Pectin | 0.10% to 10.0% |

-continued

| INGREDIENT | BY WEIGHT PERCENTAGES (%) |
|---|---|
| EMBODIMENT 2 | |
| Liquid nitrogen | 30.0% to 45.0% |
| Citronella oil | 40.0% to 55.0% |
| Gum arabic | 0.10% to 10.0% |
| EMBODIMENT 3 | |
| Liquid air | 30.0% to 45.0% |
| Wintergreen | 40.0% to 55.0% |
| Lecithin | 0.10% to 10.0% |
| EMBODIMENT 4 | |
| Liquid carbon dioxide | 35.0% to 45.0% |
| Pennyroyal oil | 40.0% to 55.0% |
| Polysorbate 20 | 0.10% to 10.0% |
| EMBODIMENT 5 | |
| Liquid nitrogen | 30.0% to 45.0% |
| Pennyroyal | 40.0% to 55.0% |
| Guar vegetable gum | 0.10% to 10.0% |
| Rose oil | 0.10% to 2.0% |

It is understood that many different combinations of ingredients can be obtained by mixing of various liquid coolant materials, essential oils and diluent carrier materials for formulating numerous embodiments using the aforementioned listing of ingredients of liquid coolant materials, essential oils, diluent carrier materials, and the optionally added fragrances for the formation of the aerosol liquid coolant spray composition 10.

Operation of the Present Invention

Figure 2:
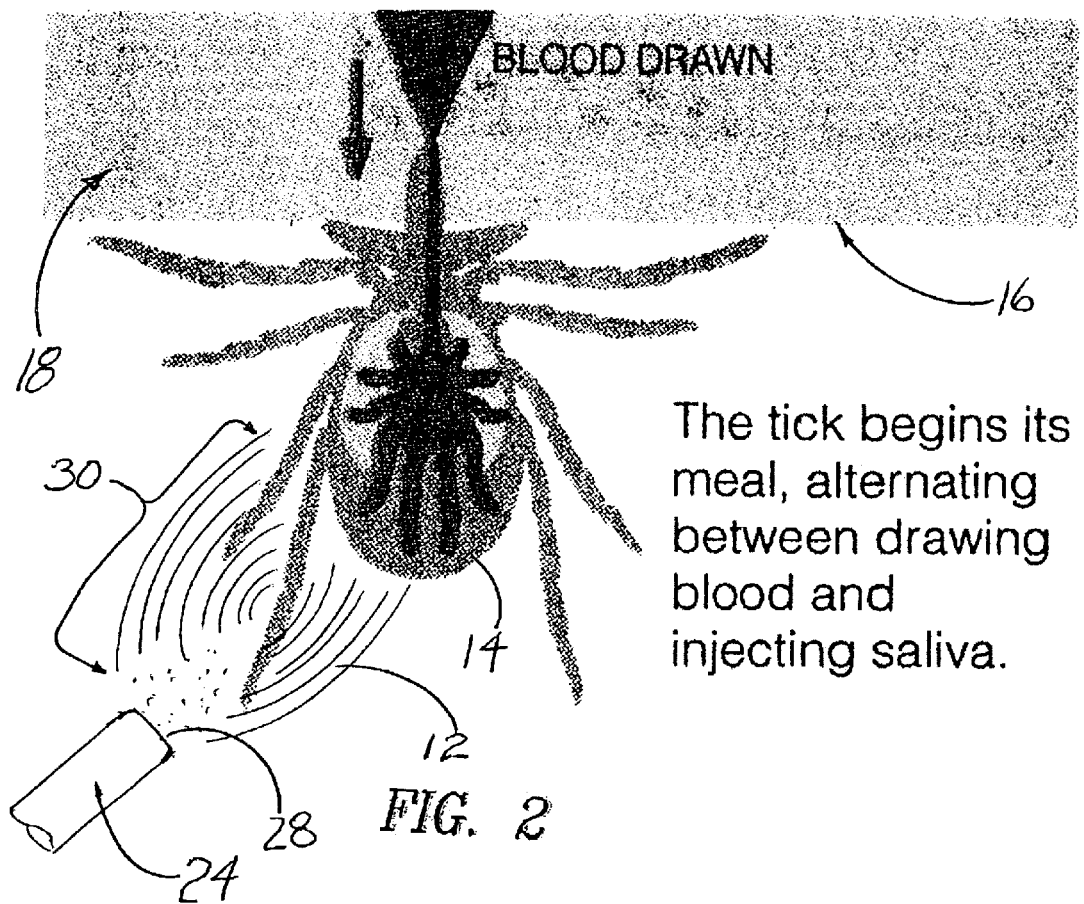
FIG. 2 is a top plan view of the aerosol coolant spray composition of the present invention showing the tip of a capillary-like extension tube spraying the aerosol liquid coolant spray on a tick attached to the surface of human skin.

The method of operation is defined by the application of an aerosol liquid coolant spray 12 to a tick 14, in an amount sufficient to effect killing and dislodgement of the tick 14 on the skin surface 16 of the users arm 18 (or other body parts), as shown in FIGS. 1 and 2 of the drawings. The composition 10 includes a liquid coolant material for cooling an essential oil. The cooled essential oil for immobilizing and killing the tick and a diluent/carrier material for emulsifying the coolant material and the essential oil within a pressurized aerosol spray cannister 20, as shown in FIG. 1 of the drawings. The coolant material is defined as a liquid that cools or freezes material by vaporization at a low temperature. The liquid coolant material includes chloroform, ether, fluorocarbon refrigerant R134, liquid air, liquid argon, liquid butane, liquid carbon dioxide, liquid DYMEL™ (dimethyl ether; E.I. DuPont de Nemours and Co. ) blend, liquid helium, liquid nitrogen, liquid oxygen, liquid propane, and liquid refrigerant compounds and other coolant formulations. (See Table 1).

More specifically, the composition 10 is an aerosol composition under pressure used to aerate the liquid coolant material and the essential oil within the small container/cannister 20. The composition 10 is dispensed through a valve 22 in the form of a spray area output 30 and can be sprayed directly on a tick 12 via a capillary-like extension tube 24 (see FIG. 2) attached to the nozzle 26 of an aerosol cannister 20 of the aerosol liquid coolant spray composition 10. The composition 10 within the cannister 20 is pressurized in a range of 10 psig to 300 psig and cannister 20 can have a metered spray area output 30. The liquid composition 10 in aerosol form having a metered spray area output 30 include those marketed by Phillips ECG Inc. These canisters 20, manufactured by American Can Co., are equipped with a variable control valve 22, manufactured by Precision Valve Co., which allows a low, medium or high spray. Each discharge of the composition 10 with the valve set on low, medium or high is approximately 1 to 2 seconds in duration with the amount of refrigerant released varying between 1 to 2 milliliters in volume.

Removal of the tick 14 from the surface of the skin 16 of the human 18 is accomplished by placing the free end 28 of the capillary-like extension tube 24 attached to the nozzle 26 of the container 20 having the aerosol liquid coolant spray composition 10 therein, directly above the tick 14, as shown in FIG. 1. The container 20 is discharged by a user or operator as necessary to kill and dislodge the tick 14 from the surface of skin 16 on arm 18. Upon the completion of spraying, the spray area output 30 covers an affected area being a circle between 3 $mm^2$ to 6 $mm^2$, as depicted in FIG. 1. The tick 14 on skin 16 is frozen, dead and dislodged. During discharge only the tick 14 is sprayed, so little or no over spray to the skin surface of the human 18 is needed. Since the composition does not directly contact the skin 16, there is no significant lowering of the skin surface 16 temperature. Final removal of the tick 14 is accomplished by picking the frozen, dead tick from the skin surface 14 on arm 18 with tweezers 32.

Advantages of the Present Invention

Accordingly, an advantage of the present invention is that is provides for a composition of an aerosol coolant spray for killing and removing ticks from human skin being dispersed from a pressurized aerosol spray cannister.

Another advantage of the present invention is that it provides for an aerosol spray composition that consists of a liquid coolant material, an essential oil and a diluent material which allows the safe, quick, painless and efficient killing and removal of ticks from human skin.

Another advantage of the present invention is that it provides for an aerosol spray composition for killing and removing ticks from human skin without any deleterious or harmful effect on the human skin of the user.

Another advantage of the present invention is that it provides for an aerosol spray composition for killing and removing ticks from an area of human skin wherein the liquid coolant material cools the essential oil which is applied to the tick so as to freeze, kill and dislodge the tick from the specific area of skin.

Another advantage of the present invention is that it provides for an aerosol spray composition for killing and removing ticks from a specific area of human skin wherein a compressible liquid coolant material and an essential oil are in aerosol form for spraying the cooled essential oil directly on the tick so as to freeze, kill and dislodge the tick from the skin of the user without freezing or damaging the skin of the user.

A further advantage of the present invention is that it provides for a pressurized aerosol coolant spray composition for killing and removing ticks from a pressurized aerosol spray cannister that can be mass produced in an automated and economical manner and is readily affordable by the consumer.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A composition of an aerosol coolant spray for killing and removing ticks from human skin, to be dispensed from a pressurized aerosol spray container, comprising:
   a) an essential oil to be cooled for immobilizing and killing a tick on the skin of a human;
   b) a liquid coolant material for cooling said essential oil in order to immobilize and kill the tick on the skin of a human; and
   c) a diluent material being used as a carrier material for emulsifying said cooled essential oil and said coolant material within the pressurized aerosol spray container.

2. A composition in accordance with claim 1, wherein said liquid coolant material is selected from the group consisting of chloroform, ether, fluorocarbon refrigerant R134, liquid air, liquid argon, liquid butane, liquid carbon dioxide, liquid dymel™ blend, liquid helium, liquid nitrogen, liquid oxygen and liquid propane.

3. A composition in accordance with claim 2, wherein said liquid coolant material is in the range of 30.0% to 45.0% by weight of said composition.

4. A composition in accordance with claim 1, wherein said liquid coolant material has a boiling point in the range of −340° F. to −20° F.

5. A composition in accordance with claim 1, wherein said essential oil is selected from the group consisting of cedar oil, citronella oil, wintergreen oil, pennyroyal, olive oil, eucalyptus oil, geranium oil, rosemary oil, peppermint oil, lavender oil, spearmint oil, pine needle oil, lemon oil, D-limonene, grapefruit oil, lavandin oil, cinnamon oil, clove oil, thyme oil, lemon grass oil, mandarin oil, tangerine oil, orange oil, citrus oil, lime oil, coriander oil, pomegranate oil, walnut oil, peanut oil, corn oil, canola oil, sunflower oil, sesame oil, linseed oil, safflower oil and terpenes.

6. A composition in accordance with claim 5, wherein said terpene is selected from group consisting of orange terpenes, lemon terpenes, mandarin terpenes, tangerine terpenes and lime terpenes.

7. A composition in accordance with claim 5, wherein said essential oil is in the range of 40.0% to 55.0% by weight of said composition.

8. A composition in accordance with claim 1, wherein said diluent material is selected from the group consisting of pectin, gum arabic, trasazapthenth, lecithin, polysorbate 20, polysorbate 60, polysorbate 80, stearic acid, glyceryl cocoate, sorbitstearate, alginate, sunflower ceramides, guar vegetable gum and xanthen vegetable gum.

9. A composition in accordance with claim 8, wherein said diluent material is in the range of 0.10% to 10.0% by weight of said composition.

10. A composition in accordance with claim 1, wherein said composition further includes a fragrance for scenting said composition.

11. A composition in accordance with claim 10, wherein said fragrance is selected from the group consisting of neroli oil, anethole, rose oil, methylene, sandal wood, musk, patchouly, citronella, eucalyptus, lemon grass, lavender, kamaus, cedarwood, geranium, chamomile and spruce.

12. A composition in accordance with claim 10, wherein said fragrance is in the range of 0.10% to 2.0% by weight of said composition.

13. A composition in accordance with claim 1, wherein said composition is pressurized in said aerosol spray cannister in the range between 10 psig to 300 psig.

14. A method of treating a human using an aerosol liquid coolant spray composition for killing and removing ticks from the skin of a human, to be dispensed from an aerosol spray cannister, the composition comprising a liquid coolant material and an essential oil, comprising the steps of:
   a) spraying a dosage of said composition on the tick in the affected area in order to freeze and kill the tick on the skin of the human;
   b) said dosage being an effective amount for freezing and killing the tick on the skin of the human; and
   c) removing said frozen and dead tick by picking the tick from the skin of the human with a suitable device.

15. A method in accordance with claim 14, wherein said step of spraying of said dosage amount being a single discharge of said aerosol spray cannister for approximately 1 to 2 seconds in duration whereby approximately 1 to 2 milliliters of said composition is released on to the affected skin area.

16. A method in accordance with claim 14, wherein said step of spraying of the affected area by said composition in an area on the skin of the human is in the range of 3 mm$^2$ to 6 mm$^2$.

17. A composition of an aerosol coolant spray for killing and removing ticks from human skin, to be dispensed from a pressurized aerosol spray cannister, comprising:
   a) an essential oil to be cooled for immobilizing and killing a tick on the skin of a human;
   b) a liquid coolant material for cooling said essential oil in order to immobilize and kill the tick on the skin of a human; and
   c) said cooled essential oil and said coolant material are aerated together within the pressurized aerosol spray cannister.

18. A composition in accordance with claim 17, wherein said liquid coolant material is selected from the group consisting of chloroform, ether, fluorocarbon refrigerant R134, liquid air, liquid argon, liquid butane, liquid carbon dioxide, liquid dymel™ blend, liquid helium, liquid nitrogen, liquid oxygen and liquid propane.

19. A composition in accordance with claim 18, wherein said liquid coolant material is in the range of 30.0% to 45.0% by weight of said composition.

20. A composition in accordance with claim 17, wherein said liquid coolant material has a boiling point in the range of −340° F to −20° F.

21. A composition in accordance with claim 17, wherein said essential oil is selected from the group consisting of cedar oil, citronella oil, wintergreen oil, pennyroyal, olive oil, eucalyptus oil, geranium oil, rosemary oil, peppermint oil, lavender oil, spearmint oil, pine needle oil, lemon oil, D-limonene, grapefruit oil, lavandin oil, cinnamon oil, clove oil, thyme oil, lemon grass oil, mandarin oil, tangerine oil, orange oil, citrus oil, lime oil, coriander oil, pomegranate oil, walnut oil, peanut oil, corn oil, canola oil, sunflower oil, sesame oil, linseed oil, safflower oil and terpenes.

22. A composition in accordance with claim 21, wherein said terpene is selected from group consisting of orange terpenes, lemon terpenes, mandarin terpenes, tangerine terpenes and lime terpenes.

23. A composition in accordance with claim 21, wherein said essential oil is in the range of 40.0% to 55.0% by weight of said composition.

24. A composition in accordance with claim 17, wherein said composition further includes a diluent material being used as a carrier material for emulsifying said cooled essential oil and said coolant material within the pressurized aerosol spray cannister.

25. A composition in accordance with claim 24, wherein said diluent material is selected from the group consisting of pectin, gum arabic, trasazapthenth, lecithin, polysorbate 20, polysorbate 60, polysorbate 80, stearic acid, glyceryl cocoate, sorbitan stearate, alginate, sunflower ceramides, guar vegetable gum and xanthen vegetable gum.

26. A composition in accordance with claim 24, wherein said diluent material is in the range of 0.10% to 10.0% by weight of said composition.

27. A composition in accordance with claim 17, wherein said composition further includes a fragrance for scenting said composition.

28. A composition in accordance with claim 27, wherein said fragrance is selected from the group consisting of neroli oil, anethole, rose oil, methylene, sandal wood, musk, patchouly, citronella, eucalyptus, lemon grass, lavender, kamaus, cedarwood, geranium, chamomile and spruce.

29. A composition in accordance with claim 27, wherein said fragrance is in the range of 0.10% to 2.0% by weight of said composition.

30. A composition in accordance with claim 17, wherein said composition is pressurized in said aerosol spray cannister in the range between 10 psig to 300 psig.

31. A composition of an aerosol coolant spray for killing and removing ticks from human skin, to be dispensed from a pressurized aerosol spray container, comprising:
a) an essential oil to be cooled for immobilizing and killing a tick on the skin of a human; and
b) a liquid coolant material for cooling said essential oil and acting as a propellant to deliver said cooled essential oil onto the tick in order to immobilize and kill the tick on the skin of a human.

32. A composition in accordance with claim 31, wherein said liquid coolant material is selected from the group consisting of chloroform, ether, fluorocarbon refrigerant R134, liquid air, liquid argon, liquid butane, liquid carbon dioxide, liquid dymel™ blend, liquid helium, liquid nitrogen, liquid oxygen and liquid propane.

33. A composition in accordance with claim 31, wherein said essential oil is selected from the group consisting of cedar oil, citronella oil, wintergreen oil, pennyroyal, olive oil, eucalyptus oil, geranium oil, rosemary oil, peppermint oil, lavender oil, spearmint oil, pine needle oil, lemon oil, D-limonene, grapefruit oil, lavandin oil, cinnamon oil, clove oil, thyme oil, lemon grass oil, mandarin oil, tangerine oil, orange oil, citrus oil, lime oil, coriander oil, pomegranate oil, walnut oil, peanut oil, corn oil, canola oil, sunflower oil, sesame oil, linseed oil, safflower oil and terpenes.

34. A composition in accordance with claim 31, wherein said composition further includes a diluent material being used as a carrier material for emulsifying said cooled essential oil and said coolant material within the pressurized aerosol spray cannister.

35. A composition in accordance with claim 34, wherein said diluent material is selected from the group consisting of pectin, gum arabic, trasazapthenth, lecithin, polysorbate 20, polysorbate 60, polysorbate 80, stearic acid, glyceryl cocoate, sorbitan stearate, alginate, sunflower ceramides, guar vegetable gum and xanthen vegetable gum.

36. A composition of an aerosol coolant spray for killing and removing ticks from human skin, to be dispensed from a pressurized aerosol spray container, comprising:
a) an essential oil to be cooled for immobilizing and killing a tick on the skin of a human
b) a liquid coolant material for cooling said essential oil and acting as a carrier to deliver said cooled essential oil on the tick in order to immobilize and kill the tick on the skin of a human.

* * * * *